Figure 1:
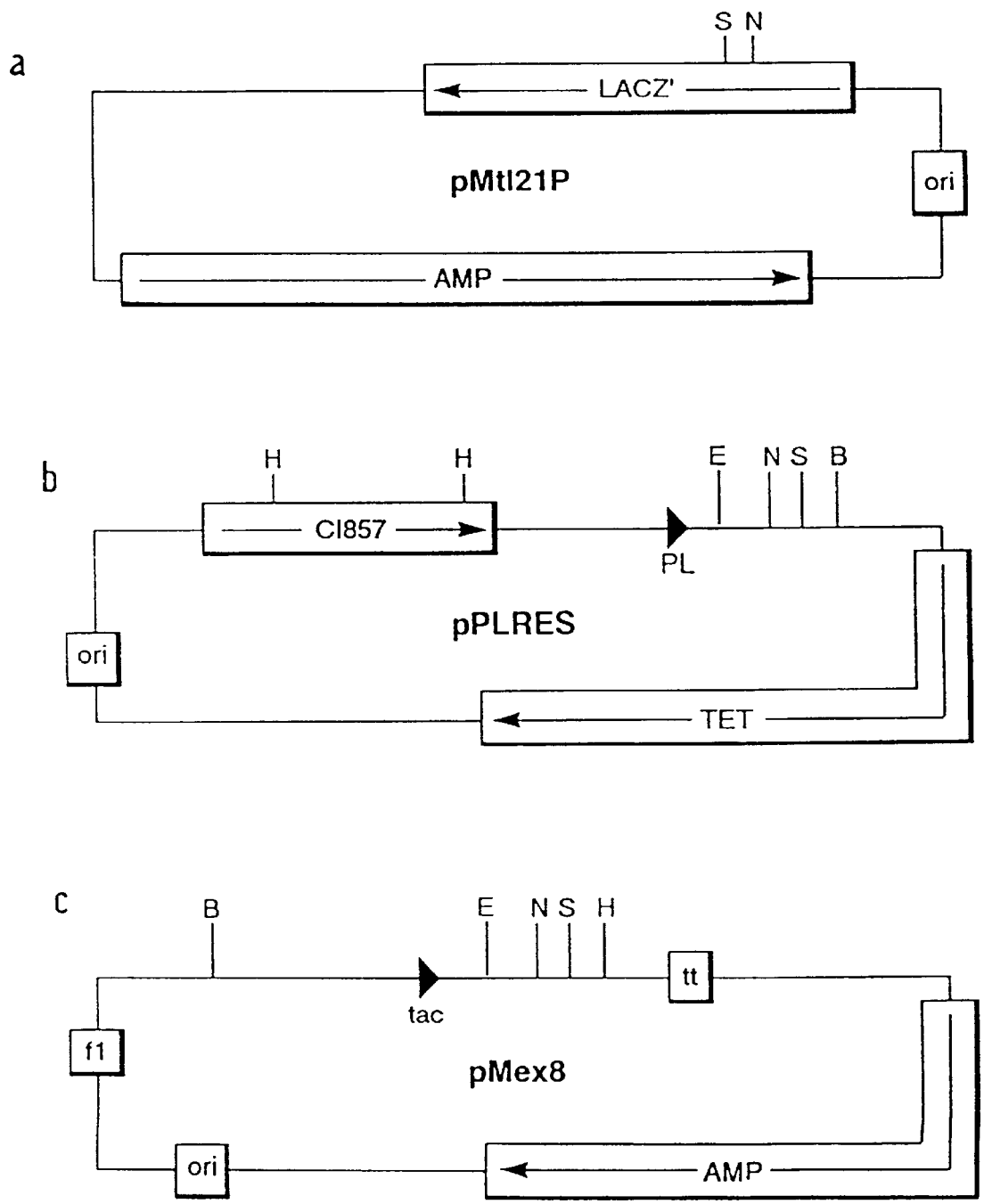

United States Patent [19]
Dawson et al.

[11] Patent Number: 6,156,544
[45] Date of Patent: Dec. 5, 2000

[54] PROCESS FOR THE PREPARATION OF N-ACETYLNEURAMINIC ACID

[75] Inventors: Michael John Dawson; David Noble; Mahmoud Mahmoudian, all of Stevenage, United Kingdom

[73] Assignee: Glaxo Group Limited, Greenford, United Kingdom

[21] Appl. No.: 09/108,975

[22] Filed: Jul. 2, 1998

Related U.S. Application Data

[63] Continuation of application No. 08/545,771, Nov. 24, 1995, abandoned.

[30] Foreign Application Priority Data

Jun. 9, 1993 [GB] United Kingdom ................ 9311873

[51] Int. Cl.$^7$ .............................. C12P 19/02; C12P 19/06; C12N 9/08
[52] U.S. Cl. ............................. 435/84; 435/105; 435/232; 536/18.7; 536/55; 536/125
[58] Field of Search ........................... 435/84, 105, 232; 536/18.7, 55.2, 125

[56] References Cited

U.S. PATENT DOCUMENTS 5,071,750 12/1991 Kragl et al. .............................. 435/94
5,472,860 12/1995 Tsukada et al. ......................... 435/105

FOREIGN PATENT DOCUMENTS 0 164 754  12/1985  European Pat. Off. .
1-0 428 947  5/1991  European Pat. Off. .
WO-A1-93 15214  8/1993  WIPO .

OTHER PUBLICATIONS

Simon et al., *J. Am. Chem. Soc.*, 1988, 110, 7159–7163.
Augé et al., *New J. Chem.*, 1988, 12, 733–744.
Kragl, Thesis, Institut für Biotechnologie, Feb. 1992, ISSN 0366–0885. Translations of p3 illustration, p. 140 Chapter 7.1, formula; p. 155 Chapter 9.5.

Kragl et al., *Angewandte Chemie*, vol. 30, No. 7, Jul. 1991, pp. 827–828.

Kuhn et al., *Justus Liebigs Ann. Chem.*, 659, Mar. 1962, pp. 156–163. (Translation included.).

Kragl et al., *Biochem. Engineering for 2001*, Conference 1992, Springer Verlag, pp. 84–87.

Schauer, *Methods in Enzymology*, vol. L, part C, Victor Ginsburg Edition, Academic Press 1978, pp. 64–89.

Aisaka et al., *Biochem. J.*, 1991, 276, pp. 541–546.

Aisaka et al., *Applied and Environmental Microbiol.*, vol. 51, No. 3, Mar. 1986. pp. 562–565.

Aisaka et al., *Biotechnology Letters*, vol. 9, No. 9, 1987, pp. 633–637.

Klenk et al., *Hoppe–Seilers Zeitschrift für physiologische Chemie*, vol. 301, 1995, pp. 235–246. (Translation included.).

Uchida et al., *Agric. Biol. Chem.*, 49(1), 1985, 181–187.

Uchida et al., *J. Biochem.*, 96, 1984, 507–522.

Kim et al., *J. Am. Chem. Soc.*, 110, 1988, pp. 6481–6486.

Augé et al., *Tetrahedron Letters*, vol. 25, No. 41, 1984, pp. 4663–4664.

Kragl, Thesis, Institut für Biotechnologie, Feb. 1992, ISSN 0366–0885, Translations of p3 illustration, p. 140 Chapter 7.1, formula; p. 155 Chapter 9.5. (pages 15–17, 78 of present application).

*Primary Examiner*—Rebecca E. Prouty
*Assistant Examiner*—Manjunath Rao
*Attorney, Agent, or Firm*—Bacon & Thomas

[57] ABSTRACT

A method for the preparation of N-acetyl-D-neuraminic acid (NANA) N-acetyl-D-glucosamine (NAG) is described.

19 Claims, 9 Drawing Sheets

FIG.2a.

```
  1  AATTCTTACA CTTAGTTAAA TTGCTAACTT TATAGATTAC AAAACTTAGG
 51  AGGGTTTTA  CCATGGTACC TTTAAACCCG GGTCGACGGA TCCTGCAGCC
101  CAGCTTGGGG ACCCTAGAGG TCCCCTTTTT TATTTTGAAT TGGGAGATCC
151  CAATTCTCAT GTTTGACAGC TTATCATCGA TAAGCTAGCT TTAATGCGGT
201  AGTTTATCAC AGTTAAATTG CTAACGCAGT CAGGCACCGT GTATGAAATC
251  TAACAATGCG CTCATCGTCA TCCTCGGCAC CGTCACCCTG GATGCTGTAG
301  GCATAGGCTT GGTTATGCCG GTACTGCCGG GCCTCTTGCG GGATATCGTC
351  CATTCCGACA GCATCGCCAG TCACTATGGC GTGCTGCTAG CGCTATATGC
401  GTTGATGCAA TTTCTATGCG CACCCGTTCT CGGAGCACTG TCCGACCGCT
451  TTGGCCGCCG CCCAGTCCTG CTCGCTTCGC TACTTGGAGC CACTATCGAC
501  TACGCGATCA TGGCGACCAC ACCCGTCCTG TGGATTCTCT ACGCCGGACG
551  CATCGTGGCC GGCATCACCG GCGCCACAGG TGCGGTTGCT GGCGCCTATA
601  TCGCCGACAT CACCGATGGG GAAGATCGGG CTCGCCACTT CGGGCTCATG
651  AGCGCTTGTT TCGGCGTGGG TATGGTGGCA GGCCCCGTGG CCGGGGGACT
```

FIG.2b.

```
701   GTTGGGCGCC ATCTCCTTGC ACGCACCATT CCTTGCGGCG GCGGTGCTCA
751   ACGGCCTCAA CCTACTACTG GGCTGCTTCC TAATGCAGGA GTCGCATAAG
801   GGAGAGCGTC GTCCGATGCC CTTGAGAGCC TTCAACCCAG TCAGCTCCTT
851   CCGGTGGGCG CGGGGCATGA CTATCGTCGC CGCACTTATG ACTGTCTTCT
901   TTATCATGCA ACTCGTAGGA CAGGTGCCGG CAGCGCTCTG GGTCATTTTC
951   GGCGAGGACC GCTTTCGCTG GAGCGCGACG ATGATCGGCC TGTCGCTTGC
1001  GGTATTCGGA ATCTTGCACG CCCTCGCTCA AGCCTTCGTC ACTGGTCCCG
1051  CCACCAAACG TTTCGGCGAG AAGCAGGCCA TTATCGCCGG CATGGGCGCC
1101  GACGCGCTGG GCTACGTCTT GCTGGCGTTC GCGACGCGAG GCTGGATGGC
1151  CTTCCCCATT ATGATTCTTC TCGCTTCCGG CGGCATCGGG ATGCCCGCGT
1201  TGCAGGCCAT GCTGTCCAGG CAGGTAGATG ACGACCATCA GGGACAGCTT
1251  CAAGGATCGC TCGCGGCTCT TACCAGCCTA ACTTCGATCA CTGGACCGCT
1301  GATCGTCACG GCGATTTATG CCGCCTCGGC GAGCACATGG AACGGGTTGG
1351  CATGGATTGT AGGCGCCGCC CTATACCTTG TCTGCCTCCC CGCGTTGCGT
1401  CGCGGTGCAT GGAGCCGGGC CACCTCGACC TGAATGGAAG CCGGGCGGCAC
1451  CTCGCTAACG GATTCACCAC TCCAAGAATT GGAGCCAATC AATTCTTGCG
```

```
1501  GAGAACTGTG AATGCGCAAA CCAACCCTTG GCAGAACATA TCCATCGCGT
1551  CCGCCATCTC CAGCAGCCGC ACGCGGCGCA TCTCGGGGGA TGATCAGCTG
1601  CCTCGCGCGT TTCGGTGATG ACGGTGAAAA CCTCTGACAC ATGCAGCTCC
1651  CGGAGACGGT CACAGCTTGT CTGTAAGCGG ATGCCGGGAG CAGACAAGCC
1701  CGTCAGGGCG CGTCAGCGGG TGTTGGCGGG TGTCGGGGCG CAGCCATGAC
1751  CCAGTCACGT AGCGATAGCG GAGTGTATAC TGGCTTAACT ATGCGGCATC
1801  AGAGCAGATT GTACTGAGAG TGCACCATAT GCGGTGTGAA ATACCGCACA
1851  GATGCGTAAG GAGAAAATAC CGCATCAGGC GCTCTTCCGC TTCCTCGCTC
1901  ACTGACTCGC TGCGCTCGGT CGTTCGGCTG CGGCGAGCGG TATCAGCTCA
1951  CTCAAAGGCG GTAATACGGT TATCCACAGA ATCAGGGGAT AACGCAGGAA
2001  AGAACATGTG AGCAAAAGGC CAGCAAAAGG CCAGGAACCG TAAAAAGGCC
2051  GCGTTGCTGG CGTTTTTCCA TAGGCTCCGC CCCCCTGACG AGCATCACAA
2101  AAATCGACGC TCAAGTCAGA GGTGGCGAAA CCCGACAGGA CTATAAAGAT
2151  ACCAGGCGTT TCCCCCTGGA AGCTCCCTCG TGCGCTCTCC TGTTCCGACC
2201  CTGCCGCTTA CCGGATACCT GTCCGCCTTT CTCCCTTCGG GAAGCGTGGC
2251  GCTTTCTCAA TGCTCACGCT GTAGGTATCT CAGTTCGGTG TAGGTCGTTC
2301  GCTCCAAGCT GGGCTGTGTG CACGAACCCC CCGTTCAGCC CGACCGCTGC
```

FIG.2c.

| | | | | | |
|---|---|---|---|---|---|
| 2351 | GCCTTATCCG | GTAACTATCG | TCTTGAGTCC | AACCCGGTAA | GACACGACTT |
| 2401 | ATCGCCACTG | GCAGCAGCCA | CTGGTAACAG | GATTAGCAGA | GCGAGGTATG |
| 2451 | TAGGCGGTGC | TACAGAGTTC | TTGAAGTGGT | GGCCTAACTA | CGGCTACACT |
| 2501 | AGAAGGACAG | TATTTGGTAT | CTGCGCTCTG | CTGAAGCCAG | TTACCTTCGG |
| 2551 | AAAAAGAGTT | GGTAGCTCTT | GATCCGGCAA | ACAAACCACC | GCTGGTAGCG |
| 2601 | GTGGTTTTTT | TGTTTGCAAG | CAGCAGATTA | CGCGCAGAAA | AAAAGGATCT |
| 2651 | CAAGAAGATC | CTTTGATCTT | TTCTACGGGG | TCTGACGCTC | AGTGGAACGA |
| 2701 | AAACTCACGT | TAAGGGATTT | TGGTCATGAG | ATTATCAAAA | AGGATCTTCA |
| 2751 | CCTAGATCCT | TTTCAGATCT | CCCGATCTTT | AGCTGTCTTG | GTTTGCCCAA |
| 2801 | AGCGCATTGC | ATAATCTTTC | AGGGTTATGC | GTTGTTCCAT | ACAACCTCCT |
| 2851 | TAGTACATGC | AACCATTATC | ACCGCCAGAG | GTAAAATAGT | CAACACGCAC |
| 2901 | GGTGTTAGAT | ATTTATCCCT | TGCGGTGATA | GATTTAACGT | ATGAGCACAA |
| 2951 | AAAAGAAACC | ATTAACACAA | GAGCAGCTTG | AGGACGCACG | TCGCCTTAAA |
| 3001 | GCAATTTATG | AAAAAAAGAA | AAATGAACTT | GGCTTATCCC | AGGAATCTGT |
| 3051 | CGCAGACAAG | ATGGGGATGG | GGCAGTCAGG | CGTTGGTGCT | TTATTTAATG |
| 3101 | GCATCAATGC | ATTAAATGCT | TATAACGCCG | CATTGCTTAC | AAAAATTCTC |
| 3151 | AAAGTTAGCG | TTGAAGAATT | TAGCCCTTCA | ATCGCCAGAG | AAATCTACGA |
| 3201 | GATGTATGAA | GCGGTTAGTA | TGCAGCCGTC | ACTTAGAAGT | GAGTATGAGT |

FIG.2d.

```
3251  ACCCTGTTTT TTCTCATGTT CAGGCAGGGA TGTTCTCACC TAAGCTTAGA
3301  ACCTTTACCA AAGGTGATGC GGAGAGATGG GTAAGCACAA CCAAAAAGC
3351  CAGTGATTCT GCATTCTGGC TTGAGGTTGA AGGTAATTCC ATGACCGCAC
3401  CAACAGGCTC CAAGCCAAGC TTTCCTGACG GAATGTTAAT TCTCGTTGAC
3451  CCTGAGCAGG CTGTTGAGCC AGGTGATTTC TGCATAGCCA GACTTGGGGG
3501  TGATGAGTTT ACCTTCAAGA AACTAATTAG GGATAGCGGT CAGTGTTTT
3551  TACAACCACT AAACCCACAG TACCCAATGA TCCCATGCAA TGAGAGTTGT
3601  TCCGTTGTGG GGAAAGTTAT CGCTAGTCAG TGGCCTGAAG AGACGTTTGG
3651  CTGATCGGCA AGTGTTCTG GTCGGCGCAT AGCTGATAAC AATTGAGCAA
3701  GAATCTTCAT CGGGGCTGCA GCCCACGATG CGTCCGGCGT AGAGGATCTC
3751  TCACCTACCA AACAATGCCC CCCTGCAAAA AATAAATTCA TATAAAAAC
3801  ATACAGATAA CCATCTGCGG TGATAAATTA TCTCTGGCGG TGTTGACATA
3851  AATACCACTG GCGGTGATAC TGAGCACATC AGCAGGACGC ACTGACCACC
3901  ATGAAGGTGA CGCTCTTAAA ATTAAGCCCT GAAGAAGGGC AGCATTCAAA
3951  GCAGAAGGCT TTGGGGTGTG TGATACGAAA CGAAG
```

FIG.2e.

FIG.4a.

```
  1  CCATGGCAAC GAATTTACGT GGCGTAATGG CTGCACTCCT GACTCCTTTT
 51  GACCAACAAC AAGCACTGGA TAAAGCCGAGT CTGCGTCGCC TGGTTCAGTT
101  CAATATTCAG CAGGGCATCG ACGGTTTATA CGTGGGTGGT TCGACCGGAG
151  AGGCCTTTGT ACAAAGCCTT TCCGAGCCGTG AACAGGTACT GGAAATCGTC
201  GCCGAAGAGG CGAAAGGTAA GATTAAACTC ATCGCCCACG TCGGTTGCGT
251  CAGCACCGCC GAAAGCCAAC AACTTGCGGC ATCGGCTAAA CGTTATGGCT
301  TCGATGCCGT CTCCGCCGTC ACGCCCGTTCT ACTATCCTTT CAGCTTTGAA
351  GAACACTGCG ATCACTATCG GGCAATTATT GATTCGGGCGG ATGGTTTGCC
401  GATGGTGGTG TACAACATTC CAGCCCCTGAG TGGGGTAAAA CTGACCCTGG
451  ATCAGATCAA CACACTTGTT ACATTGCCCTG GCGTAGGTGC GCTGAAACAG
501  ACCTCTGGCG ATCTCTATCA GATGGAGCAG ATCCGTCGTG AACATCCTGA
551  TCTTGTGCTC TATAACGGTT ACGACGAAAT CTTCGCCCTCT GGTCTGCTGG
601  CGGGCGCTGA TGGTGGTATC GGCAGTACCT ACAACATCAT GGGCTGGGCGC
```

```
651  TATCAGGGGA TCGTTAAGGC GCTGAAAGAA GGCGATATCC AGACCGCGCA
701  GAAACTGCAA ACTGAATGCA ATAAAGTCAT TGATTTACTG ATCAAAACGG
751  GCGTATTCCG CGGCCTGAAA ACTGTCCTCC ATTATATGGA TGTCGTTTCT
801  GTGCCGCTGT GCCGCAAACC GTTTGGACCG GTAGATGAAA AATATCTGCC
851  AGAACTGAAG GCGCTGGCCC AGCAGTTGAT GCAAGAGCGC GGGTGAGTCG
901  AC
```

FIG.4b.

| Sequence | Primer Number |
|---|---|
| 5'-CGCCGAAGAGGCGAAAGGTA-3' | 1 |
| 5'-CCAGCCCCTGAGTGGGGTAAA-3' | 2 |
| 5'-TGGGCTGGGCGCTATCAGGGG-3' | 3 |
| 5'-GCGCGGTCTGGATATCGCCT-3' | 4 |
| 5'-AGGCAATGTAACAAGTGTGT-3' | 5 |
| 5'-GCGGTGCTGACGCAACCGAC-3' | 6 |

FIG.5.

PROCESS FOR THE PREPARATION OF N-ACETYLNEURAMINIC ACID

This application is a Continuation of nonprovisional application Ser. No. 08/545,771 filed Nov. 24, 1995 now abandoned.

The present invention relates to the preparation of N-acetyl-D-neuraminic acid.

N-Acetyl-D-neuraminic acid (NANA) is a sialic acid which occurs naturally as a component of complex mucoid substances such as mucolipids and mucoproteins and also as a component of oligosaccharides found for example in milk.

NANA is a useful starting material for compounds of interest as therapeutic agents. However, NANA is currently available only in limited quantities and there is a need for processes for its preparation from simple, widely available starting materials. The present invention relates to a method for the preparation of NANA from N-acetyl-D-glucosamine (NAG), and pyruvic acid.

International Patent Application No. 93/15214 (published Aug. 5, 1993) discloses a one-pot procedure for the preparation of NANA by treatment of NAG with pyruvic acid and NAN lyase under alkaline conditions.

European Patent Application No. 0428947 discloses a one-pot procedure for the preparation of NANA by treatment of NAG with NAG-2-epimerase, NANA lyase and pyruvate.

The present invention provides in a first aspect a process for the preparation of NANA comprising the steps of:
1. converting NAG to N-acetyl-D-mannosamine (NAM) to yield an equilibrium mixture of NAG/NAM;
2. selectively removing NAG from the equilibrium mixture;
3. reacting NAM with pyruvate in the presence of NANA aldolase; and
4. isolating the thus-produced NANA.

Conversion of NAG to NAM is effected by base-catalysed epimerisation. This reaction may be effected by treating NAG with a base, for example an alkali metal hydroxide such as sodium or potassium hydroxide or a quaternary ammonium ion exchange resin in the hydroxyl form such as Duolite A113 (OH$^-$), in an aqueous medium, for example water, at ambient or elevated temperature, for example 20 to 50° C., preferably about 25 to 35° C. Epimerisation may be carried out at different concentrations of NAG, but preferably at its saturation concentration. The reaction is continued until equilibration between NAG and NAM is reached. Reaction times will vary with the temperature and pH of the reaction but for example at about 25° C. and about pH 11 equilibration is achieved at about 20–60, for example about 40, hours, or at about 32° C. and >pH 11 equilibration is achieved at about 12–20, for example about 16, hours. The ratio of NAM to NAG on equilibration is typically about 1:4 by weight.

The NAM/NAG mixture is enriched in NAM by selective removal of NAG. This enrichment may be carried out in a variety of ways. Thus, the NAM/NAG mixture may be concentrated to a residue by evaporation or spray drying. This residue may then be extracted with an organic solvent such as a lower alcohol, preferably methanol, in an amount just sufficient to dissolve the NAM present. Removal of insoluble NAG gives a solution rich in NAM. Alternatively, the NAM/NAG mixture, preferably having a high starting concentration of NAG or optionally concentrated to achieve a high concentration of NAG, may be treated with a suitable organic solvent such as a lower alcohol, preferably isopropanol, in the ratio of 1 volume of epimerisation mixture to 5 to 10 volumes, preferably about 6 volumes, of isopropanol, and preferably at a temperature of from 15° to 30° C., such as 200 to 25° C. After removal of crystalline NAG the residual solution is rich in NAM. This solution may be further enriched by evaporation of the isopropanol/water azeotrope, preferably with an isopropanol feed to the evaporator, to give a second crop of crystalline NAG. Organic solvent is removed from the NAM-enriched solutions before presenting them to the next step of the process at the preferred concentration in water. By this means the ratio of NAM to NAG may be increased to about 1.5:1 to 10:1, typically, on large scale, 1.5:1 to 4:1. NAG recovered during the enrichment process maybe reused in the epimerisation step, optionally in admixture with fresh NAG.

When a base such as sodium hydroxide is used in the epimerisation step, the reaction mixture is neutralised using, for example, an acid resin [e.g. Amberlite 200 (H$^+$) or IR120 (H$^+$)] or a suitable acid (e.g. acetic acid) prior to reaction with pyruvate.

In the third step of the process the NAM/NAG mixture enriched in NAM is incubated with pyruvate (e.g. sodium pyruvate) in the presence of NANA aldolase, for example Escherichia coli NANA aldolase (EC4.1.3.3).

NANA aldolase is a known enzyme [cf D Comb and S Roseman, J Biol Chem 235, 2529–2537 (1990)] and may be obtained, for example, either from a naturally occurring NANA aldolase-producing strain of *E. coli* (including constitutive mutant strains) or from an overexpressing recombinant strain of *E. coli*. Preferably the NANA aldolase is obtained from an over-expressing recombinant strain of *E. coli*. In particular the NANA aldolase is obtained from either of the recombinant *E. coli* strains TG1[pMexAld] and TG1 [pPLAld], described hereinafter and forming further aspects of the present invention.

The NANA aldolase may be used in free form or, preferably, immobilised to allow reuse of the enzyme. Immobilisation may be carried out for example by mixing untreated cell homogenate or partially purified extracts of a NANA aldolase-producing strain in a suitable buffer with an activated resin such as Eupergit C (Rohm Pharma) and either stirring or standing with occasional mixing for 2 to 15 days. The immobilised beads can then be recovered after use in the reaction by filtration and re-used. Other immobilisation procedures known in the art can also be utilised, including immobilisation of the enzyme by containment within a hollow fibre or membrane reactor.

The conversion of NAM to NANA is carried out in aqueous medium at a pH of 6.0 to 9.0, for example 7 to 8, at a temperature of 5° to 60 C, for example about 20° to 30° C., for from about 2 to 48 hours. The reaction is terminated when a substantial amount of NAM, up to about 95%, is converted to NANA.

Use of NAM-enriched NAM/NAG mixtures allowing for higher concentrations of NAM offers a number of advantages for NANA production, including a faster reaction, increased productivity and a lower requirement of pyruvate. Most significantly, this results in a high concentration of NANA and low concentrations of NAG and pyruvate which greatly simplifies the isolation process.

When an enriched NAM/NAG mixture is used at high concentration the pyruvate: NAM starting molar ratio should be about 1.5 to 2.5:1. If an equilibrium mixture is employed with a lower NAM concentration a higher molar excess of pyruvate, e.g. about 5 times, is required.

In the fourth step of the process of this invention, the NANA may be isolated from the reaction mixture by any conventional physical, chemical or physiochemical method, for example by crystallisation, chromatographic separation and the like. The chosen method of isolation will be determined primarily by the concentration of NANA in the final reaction mixture and by the ratio of NANA to pyruvate and NAG. Where an enriched NAM/NAG mixture has been used at high concentration with a pyruvate:NAM starting molar ratio of about 1.5–2.5:1 and concentration in the reaction mixture is (or can be concentrated to) about 150 g/liter then simple crystallisation from the reaction mixture, e.g. by addition of from 4 to 8, preferably 6, volumes of acetic acid, is effective.

When the NANA concentration in the reaction mixture is below 150 g/liter, it may be necessary to remove other components from the reaction mixture before NANA is itself isolated.

Sodium ions may conveniently be removed by passing the reaction mixture through an ion exchange resin such as Amberlite 200 ($H^+$) or IR120 ($H^+$). This reduces the pH of the reaction mixture to about 2.

Pyruvate may be selectively removed from the mixture after reaction with metabisulphite anion by absorption of the hydroxysulphonic acid formed onto an ion exchange resin. The reaction and adsorption may be conveniently carried out in one stage by passage of the acidified mixture through a column of quaternary ammonium ion exchange resin such as Duolite A113 in the bisulphite form. Any leached bisulphite ions in the effluent from this column may be precipitated by addition of calcium ions.

NAG may be separated from NANA by retention of NANA on a suitable ion exchange resin e.g. Duolite A113 in the acetate form. NAG passes-through the resin and may be recycled through the process after equilibration to a NAG/NAM mixture as above. The NANA may be eluted from the column with a suitable acid or salt such as formic acid or preferably sodium acetate. NANA may be crystallised from the effluent after suitable concentration by addition of a co-solvent such as acetonitrile or preferably acetic acid. In the case of salt elution of NANA from the ion exchange column it may be preferable to remove cations before any concentration and crystallisation by treatment of the solution with an ion exchange resin in the acid form e.g. Amberlite 200 (H+) or IR120 (H+) as above.

Crystalline NANA produced by these processes may be further treated in a number of ways. The level of solvent in the product may be reduced by drying at an elevated temperature e.g. 30° to 60° in vacuo. Alternatively, the crystalline material may be slurried in acetone containing a small amount of water (eg about 0.5%) and the crystals recovered by filtration and dried as before. The needle crystals produced by the acetic acid crystallization may be converted either with or without prior desolvation to rhomboid crystals by adding slowly to water (eg about 1 weight per volume). After stirring for an appropriate period (eg about 30 min) the crystallisation can be enhanced by the addition of acetone (eg about 8 to 9 volumes per weight initial crystals). The rhomboid crystals can be recovered by filtration, washed with acetone and dried as before. If required the rhomboid crystals can be recrystallised by repeating this procedure. NANA can thus be isolated in highly pure form.

The preparation of overexpressing recombinant *E. coli* NANA aldolase producing strains is described in Example 1 hereinafter.

In the Figures:

FIG. 1 shows Maps of Plasmids
a) pMtl21 P contains a multiple cloning site within the lacZ' gene for which only the NcoI and SalI sites are indicated).
b) pPLRES contains the bacteriophage lambda phage leftward promoter (PL) and the bacteriophage lambda phage $C_{1857}$ repressor gene. The gene product from $C_{1857}$ is a temperature sensitive repressor of the PL promoter. Transcription from PL is induced by a shift from the permissive temperature to the non permissive temperature (usually 30° C. to 40–42° C.).
c) pMex8 contains the hybrid tac promoter which can be repressed by the product of a host cell encoded lacI gene. Repression is removed by the presence of IPTG. This plasmid also contains the rrnB transcription terminator (tt) adjacent to the tac promoter. In addition to the ColE1 origin of replication this plasmid contains the F1-intergenic region (f1).

AMP, β-lactamase gene; TET, tetracycline resistance gene; ori, origin of replication; B, BamHI; E, EcoRI; H, HindIII; N, NcoI; S, SalI. Maps are not drawn to scale.

FIGS. 2a–e shows the sequence of Plasmid pPLRES.

The sequence of one strand of plasmid pPLRES is shown, starting at the first A of the unique EcoRI site (GAATTC) and proceeding in a rightward direction (5' to 3') around the plasmid as represented in FIG. 1b. The circular plasmid is written as a linear sequence.

Figure 3:
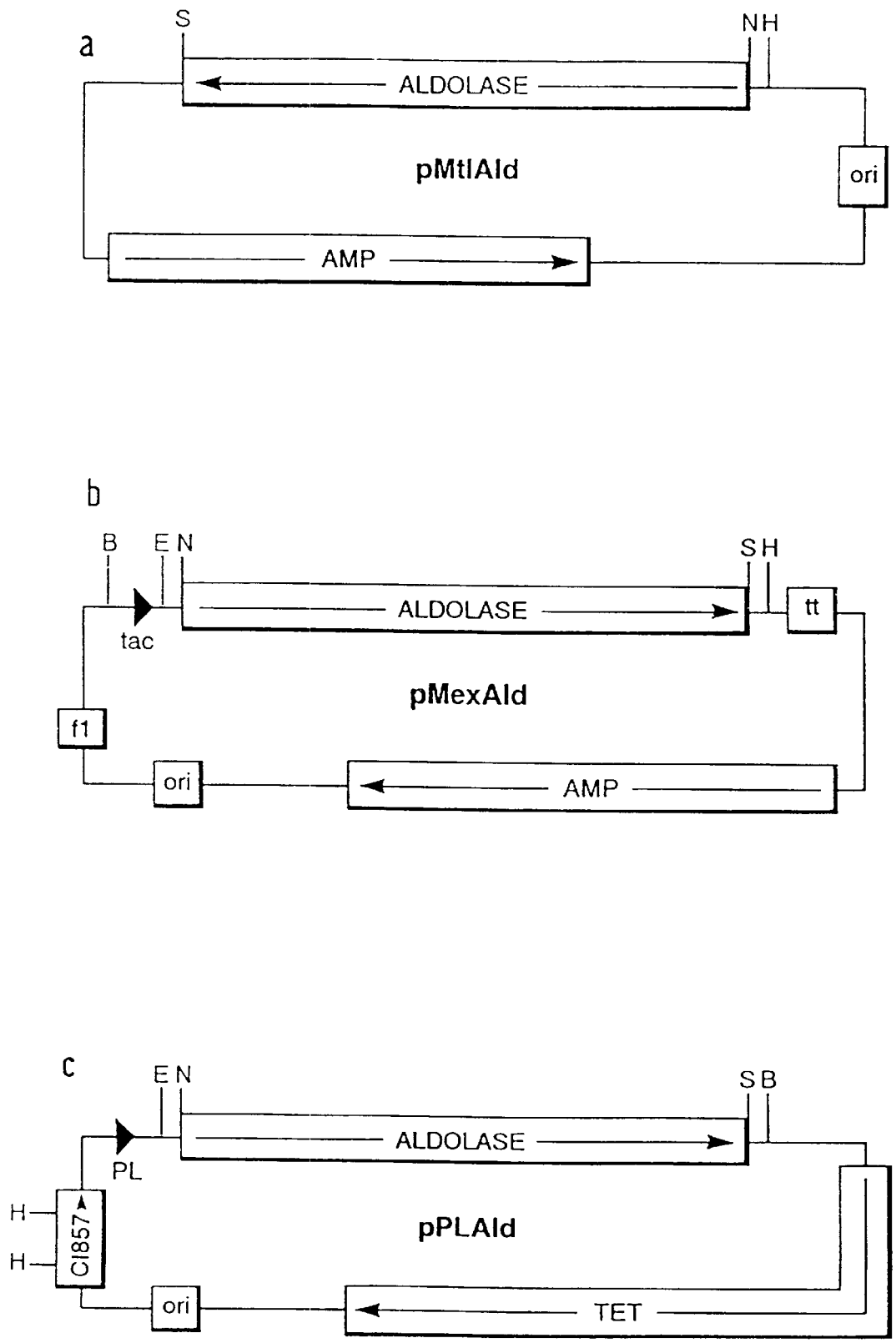

FIG. 3 shows maps of Plasmids containing the Aldolase sequence
a) pMtlAld.
b) pMexAld
c) pPLAJd AMP; β-lactamase gene; TET, tetracycline resistance gene; ori, origin of replication f1, f1-intergenic region; tt, rrnB transcription terminator; triangle, promoter used to direct transcription of the aldolase sequence; tac, hybrid tac promoter; PL, bacteriophage lambda phage leftward promoter; Cl857, bacteriophage lambda phage temperature sensitive repressor gene; B, BamHI; E, EcoRI; H, Hind III; N, NcoI; S, SalI. Maps are not drawn to scale.

FIGS. 4a–b shows the sequence of the cloned Aldolase fragment

The sequence includes the NcoI site (CCATGG) and the SalI site (GTCGAC) flanking the aldolase encoding sequence. The coding strand only is shown. The translation initiation codon (ATG) is located at bases 3 to 5.

FIG. 5 shows Aldolase sequencing primers

Six synthetic DNA primers were synthesised, based on the published aldolase sequence (Y Ohta et al, Nucleic Acids Research 1985, 13, 8843–8852) and used to sequence regions of the cloned aldolase gene.

The invention is illustrated by the following examples which are not intended as a limitation thereof. All temperatures are in ° C.

EXAMPLE 1

*E. Coli*TG1[pMexAId] and *E. Coli*TG1[pPLAid]
1. Materials

X-Gal (5-bromo-4-chloro-3-indolyl-β-D-galactopyranoside) and enzymes NcoI, SaiI, T4DNA ligase were obtained from Boehringer Mannheim UK (Diagnostics and Biochemicals). Taq polymerase was obtained from Promega Corporation UK. Geneclean was obtained from Bio 101, Inc. La Jolla Calif. USA. IPTG isopropyl-β-D-thiogalactopyranoside) was obtained from United States Biochemical. dATP, dCTP dGTP and dTTP, M13mp18 and M13mp19 were obtained from Pharmacia. [$\alpha^{33}P$] dATP and [$\alpha^{35}S$] dATP were obtained from Amersham International PLC.

2. Plasmids and *E. coli* Strains
a) pMtl21 P
Obtained from Dr N P Minton [ref Chambers S P, Prior S E, Barstow D A, Minton N P, 1988 Gene 68 139–149].

b) p Mex8
Obtained from MEDAC. Gesellshaft fur Klinische Spezi älpraparate mbfl Fehlandtstrasse 3. D-2000 Hamburg 36.

c) pPLRES
pPLRES was constructed with the sequence shown in FIG. 2.

d) *E. coli* TGI
Obtained from Amersham International plc. Geneotype: K12 Δ (lac-pro), supE, thi, hsd D5, F' tra D36, proA$^+$B$^+$, lacI$^q$, lacZΔM15.

e) *E. coli* C600
F$^-$e14 (mcrA$^-$) hr-1, leuB2, thi-1, lacY, supE$_{44}$, rfbD1, fhuA21.

| Growth of Strains | | |
|---|---|---|
| C600 | LB | 37° C. |
| TG1 | MGT | 37° C. |
| TG1/pMex8 | MGT amp | 37° C. |
| TG1/pMexAld | MGT amp | 37° C. |
| TG1/pPLcddPCR | LBtet | 30° C. |
| TG1/pPLAld | LBtet | 30° C. |
| TG1pMtl21P | LB amp | 37° C. |

| Media | |
|---|---|
| LB (per litre) | |
| NaCl | 10 g |
| Yeast extract | 5 g |
| Bactotryptone | 10 g |
| pH 7.0 | |

| Minimal Salts (per litre) | |
|---|---|
| K$_2$HPO$_4$ | 7 g |
| KH$_2$PO$_4$ | 3 g |
| MgSO$_4$.7H$_2$O | 0.25 g |
| (NH$_4$)$_2$SO$_4$ | 1 g |
| Tri-sodium citrate | 0.5 g |
| pH 7.0 | |

MGT
Minimal salts supplemented with:
0.4% w/v glucose
0.002 mg/ml thiamine HCl
MGTC
MGT supplemented with 100 ml/liter of 20% w/v casamino acids solution LB and MGT agar plates contained media supplemented with 1.5% w/v agar Antibiotic supplements were at final concentration of:
100 μg/ml ampicillin (amp)
5 μg/ml tetracycline (tet)

4. Methods a) DNA manipulation including ligations and transformation of *E. coli* strains were performed essentially as described by Maniatis et al. Molecular cloning, Cold Spring Harbour New York 1982. Transformation of pPLRES derived ligations were carried out by the standard procedure except that heat shock was for 5 minutes at 34° C. and the incubation of heat shocked cells in non-selective media was at 30° C. rather than at 37° C.

b) Restriction endonuclease digestions were performed using conditions recommended by the suppliers.

c) The nucleotide sequence of the cloned aldolase gene was determined by the M13 dideoxy sequencing method using a Sequenase kit and [α$^{33}$P]dATP or [α-$^{33}$S]dATP.

d) Purification of DNA Fragments
Fragments of DNA were purified after electophoresis through agarose gel by means of Geneclean glass milk as described by the supplier.

e) Preparation of Synthetic DNA Sequences
Synthetic DNA was prepared by means of Biosearch model SAMI (trade mark) DNA synthesiser using b-cyanoethyl phosphoramidites (N D Sinha et al, Nucleic Acid Res., 1984 12, 4539).

f) Amplification Reaction
The amplification reaction contained 1 mg genomic DNA, 1 unit Taq polymerase, 1× Promega Taq buffer 50 pmol each DNA primer, 0.0125 mM each of dATP, dCTP, dGTP and dTTP in a 0.1 ml final volume. The reaction was carried out in a Techne PHC-3 Thermal cycler. 1 cycle of 90° C., 10 minutes, 50° C. 20 minutes then 3 cycles of 50° C., 1 minute, 70° C., 2 minutes, 92° C., 1 minute then 27 cycles of 50° C., 1 minute, 70° C., 2 minutes, 92° C., 10 seconds then 1 cycle of 50° C., 1 minute, 70° C., 5 minutes, then cooled to 4° C.

5. Cloning of Aldolase Encoding Sequence from *E. coli* C600 a) Genomic DNA was prepared from 5ml of an overnight culture of *E. coli* C600, grown in LB at 37° C., by the method described in Current Protocols in Molecular Biology, Vol1 page 2.4.1 (Eds F M Ausubel et al).

b) The aldolase gene was specifically amplified from the *E. coli* C600 genomic DNA using a Taq polymerase reaction primed by synthetic DNA sequences Ald/PCR/1 and Ald/PCR/2: the design of these primers was based on the published aldolase gene sequence (Y. Ohta et al, Nucleic Acids Research, 1985, 13, 8843–8852).

Ald/PCR/1
5'-GACGCTA<u>CCATGG</u>CAACGAATTTACGTGGCG-3
         NcoI
Ald/PCR/2
5'-GATCCA<u>GTCGAC</u>TCACCCGCGCTCTTGCATC-3
      SalI

The DNA fragment produced by this reaction contained the aldolase encoding sequence flanked by NcoI and SalI sites introduced from the sequence in the primer. The NcoI site (CCATGG) was placed at the position corresponding to the translation initiation codon. The SalI site (GTCGAC) was placed immediately 3' to the termination codon (TGA).

c) The aldolase gene fragment was digested with NcoI and SalI and purified by means of Geneclean.

The purified aldolase fragment was ligated into plasmid pMtl21P digested with NcoI and SalI. The ligation reaction was used to transform *E. coli* TG1 to ampicillin resistance. An ampicillin resistant colony with a white phenotype on LBagar plates supplemented with ampicillin (0.1 mg/ml), XgaI (0.08 mg/ml) and IPTG (0.2 mM) was isolated that contained the aldolase sequence. The plasmid in this clone was called pMtlAld (FIG. 3a).

d) The aldolase fragment from pMtlAid was transferred into M13mp18 and M13mp19 as a BamHI-HindIII fragment and the sequence determined and confirmed to be aldolase by comparison with the sequence published by Y Ohta et al Nucleic Acids Res. 1985 13, 8843. The sequence of the cloned aldolase fragment in pMtlAld is shown in FIG. 4. Primers used to determine the sequence were those shown in FIG. 5 and the −40 primer provided with the Sequenase kit.

6. Cloning of Aldolase Gene into E. coli Expression Plasmids a) Plasmid pMtlAld was digested with NcoI and SalI and the aldolase fragment purified by Geneclean.
b) Plasmid pMex8 was digested with NcoI and SalI and the 3.6 kilobase pair (Kbp) fragment purified by Geneclean.
c) Plasmid pPLRES was digested with NcoI and SalI and the 3.96 kbp fragment purified by Geneclean.
d) The aldolase fragment from a) was ligated into the purified pMex8 fragment from b) and the ligation reaction used to transform E. coli TG1 to ampicillin resistance. A clone was isolated that contained the aldolase gene correctly inserted in the pMex8 fragment. The plasmid in this clone was called pMexAld (FIG. 3b).
e) The aldolase fragment from a) was ligated into the purified pPLRES fragment from c) and the ligation reaction used to transform E. coli TGI to tetracycline resistance. A clone was isolated that contained the aldolase gene correctly inserted into the pPLRES fragment. The plasmid in this clone was called pPLAld (FIG. 3c).

EXAMPLE 2

Production of NANA Aldolase 0.5 ml of a frozen suspension of E. coli TG1 [pMexA d] was used to inoculate 2×400 ml of MGTA broth in 2 liter flasks.

| MGTA | |
|---|---|
| INGREDIENT | g/L |
| $K_2HPO_4$ | 7 |
| $KH_2PO_4$ | 3 |
| $MgSO_4.7H_2O$ | 0.1 |
| $(NH_4)_2SO_4$ | 1 |
| Tri-sodium citrate | 0.5 |

Distilled water. Natural pH. Sterilise for 120°/15 mins.

Added post-autoclaving:

| | |
|---|---|
| *Thiamine.HCl | 0.002 |
| Glucose | 4 |
| *Ampicillin | 0.05 |

*filter sterilised.

The ampicillin solution was prepared fresh and added immediately prior to inoculation.

The flasks were incubated overnight at 37° C. on a rotary shaker operated at 250 rpm with a 5 mm diameter orbital motion. Each flask was used to inoculate 45 liters of MGTCA/1 or MGTCA/2 broth in a 70 liter fermenter.

| | MGTA/1 | | MGTCA/2 | |
|---|---|---|---|---|
| INGREDIENT | g/L | g/45L | g/L | g/45L |
| $K_2HPO_4$ | 10.5 | 472.5 | 14.0 | 630 |
| $KH_2PO_4$ | 4.5 | 202.5 | 6.0 | 270 |
| $MgSO_4.7H_2O$ | 0.15 | 6.75 | 0.2 | 9 |
| $(NH_4)_2SO_4$ | 1.5 | 67.5 | 2.0 | 90 |
| Tri-sodium citrate | 0.75 | 33.75 | 1.0 | 45 |
| Casamino acids (Difco) | 20.0 | 900 | 20.0 | 900 |
| PPG 200 (KKGreef) | | 25 | | 25 |

Distilled water. Natural pH. Fermenters were sterilised at 121° C./30 mins.

Added post-autoclaving:

| | MGTA/1 | | MGTCA/2 | |
|---|---|---|---|---|
| INGREDIENT | g/L | g/45L | g/L | g/45L |
| Glucose | 6 | 270 | — | — |
| Glycerol | — | — | 8 | 360 |
| *Thiamine.HCl | 0.002 | 0.09 | 0.002 | 0.09 |
| *Ampicillin | 0.05 | 2.25 | 0.05 | 2.25 |

*Filter sterilised. The ampicillin solution was prepared fresh and added immediately prior to inoculation.

Added two hours after inoculating:

| | | | | |
|---|---|---|---|---|
| Isopropyl β-D-thio-galactoside (IPTG) | 0.024 (0.1 mM) | 1.07 | 0.024 (0.1 mM) | 1.07 |

On-demand:
PPG200 (KKGreef)

The cultures were incubated for 26 hours at 37° C., with stirring at 500 rpm and 451 pm airflow. IPTG was added to induce aldolase production 2 hours after inoculation.

The two fermentation broths were bulked and harvested by continuous centrifugation (Sharples) to obtain 1.75kg of wet cell paste. This was suspended in 5.5 L of lysis buffer and homogenised by 3 passes through a Manton-Gaulin homogeniser (8000 psi) to obtain the crude extract.

| LYSIS BUFFER | |
|---|---|
| INGREDIENT | CONCENTRATION |
| $KH_2PO_4$ | 20 mM |
| $K_2HPO_4$ | 20 mM |
| ethylenediamine tetra acetic acid (EDTA) | 1 mM |
| dithiothreitol (DTT) | 1 mM |
| phenylmethanesulphonylfluoride | 1 mM |

The aldolase enzyme was immobilised by mixing the crude extract with 1.27 kg of Eupergit-C beads (Rohm Pharma) and allowing the mixture to stand at room temperature with occasional stirring for 10 days. The beads (wet weight 4.44 kg) were washed in buffer until the $A_{280}$ Of the supernatant was below 0.1, and stored in the same, but without NaCl, at 4° C.

| WASH BUFFER (pH 7.0) | |
|---|---|
| INGREDIENT | CONCENTRATION |
| Tris-HCl | 100 mM |
| NaCl | 500 mM |
| EDTA | 1 mM |

-continued

WASH BUFFER (pH 7.0)

| INGREDIENT | CONCENTRATION |
|---|---|
| DTT | 1 mM |
| p-hydroxybenzoic acid ethyl ester | 3 mM |

EXAMPLE 3

Production of NANA

2kg N-acetyl-D-glucosamine (NAG) and 44 g sodium hydroxide were dissolved in 20 liters of water and the solution allowed to stand at room temperature. After 66 hours, 1 liter of IR120 (H$^+$) (Rohm and Haas) was added to reduce the pH below 7 and then the resin removed by filtration. Three batches were epimerised to give a bulk solution containing N-acetyl-D-mannosamine (NAM) and NAG in the approximate ratio of 1:4.

50 liters of the epimerised mixture and 2.5 kg of sodium pyruvate were added to a 70 liter vessel. The pH was adjusted to 7.4 with sodium hydroxide and the reaction started by the addition of 4.4 kg of washed immobilised enzyme beads from Example 2. The reaction mixture was stirred at 133 rpm with a single turbine impeller, and the temperature maintained at 20° C. The reaction was allowed to proceed for 27 hours after which approximately 90% of the NAM had been converted to NANA.

The immobilised enzyme beads were removed from the reaction mixture by vacuum filtration through filter cloth on a pan filter, washed with 7 L distilled water and the washes bulked with the filtrate. Sodium ions were removed from the filtrate by passage through an IR120.(H$^+$) resin column (15 L), at a flow rate of 2 bed volumes (bv) hr.$^{-1}$. NAG, NAM, NANA and pyruvate passed straight through the column. Residual NAG, NAM, NANA and pyruvate were washed from the column with 1 bv of distilled water, at the same flow rate, and bulked with the column effluent. Pyruvate was absorbed from the effluent solution onto a Duolite A113 PLUS (HSO$_3$-) (Rohm and Haas) column (16.7 L) for column regeneration method see below). NAG, NAM and NANA passed through the column; residual amounts were removed by washing with 1 bv of distilled water and bulked with the column effluent. Sodium ions remaining in solution were removed by treating the effluent with 2.2 kg (wet weight) of IR120.(H$^+$) resin. The resin was removed by vacuum filtration through Whatman 54 filter paper and washed with 2 L of distilled water, the washes were bulked with the filtrate. Excess HSO$_3$- was precipitated by the addition of 600 g of to solid calcium hydroxide, the solid being recovered by filtration as before. Calcium ions were removed by the batchwise addition of 3 kg (wet weight) of IR120.(H$^+$) resin, the resin being recovered by filtration as before.

NANA was adsorbed from the filtrate onto a Duolite A113 PLUS.(OAc-) column (25 L). NAG and NAM passed straight through the column and were washed clear with distilled water. NANA was eluted from the column with 1M-sodium acetate solution. The fraction eluting between 0.5–2 bv was bulked and excess Na$^+$ was removed on a column of IR120. (H$^+$) resin (37.5 L). The NANA was washed from the column with 0.5 bv distilled water and bulked with the column effluent.

The effluent was concentrated to approximately 100 g.L$^{-1}$ NANA on a Balfors wiped film evaporator, vacuum filtered through Whatman 54 filter paper to remove insoluble material and the NANA crystallised by the addition of 9 volumes of acetonitrile. The solid was recovered by filtration as before and washed with fresh acetonitrile, before drying to constant weight over P$_2$O$_5$ in a vacuum oven. This solid (838 g) was approximately 80% pure by HPLC.

The above solid (818 g) was recrystallised by redissolving in water (at 250 g.L$^{-1}$) and adding 5 volumes of glacial acetic acid. The solid was recovered after 3 days at 4° C. by vacuum filtration through Whatman 54 filter paper and washed with 5 L of acetonitrile. The solid was dried under vacuum at a temperature of 80° C. to constant weight. Final weight 620.4 g, purity by HPLC 95.4%.

Regeneration of A113 PLUS.HSO$_3$- Resin

The resin was supplied in the Cl$^-$ form. The following solutions were then passed through the column.

1. New Resin

Stage i) 0.5M-Sodium hydroxide to give an effluent pH>12 ii) Distilled water to neutral pH iii) 0.5M-HCl to give an effluent pH<2 iv) Distilled water to neutral pH v) 0.5M sodium metabisulphite solution (2 bv)

vi) Distilled water to remove excess Na$_2$S$_2$O$_5$

2. Used Resin

For used resin only stages v) and vi) were required.

EXAMPLE 4

Production of NANA (i) Preparation of NAM-enriched Mixtures

A solution of NAG (1.75 kg) and sodium hydroxide (38 g) in water (4.37 L) was incubated at 25° for 40 hr. Amberlite 200 (H$^+$) resin (800 ml) was added to reduce the pH below 7 and the resin removed by filtration. 2×1 L aliquots of the resulting filtrate were treated as follows:

a) A 1 L portion was evaporated to give an oily solid. This was stirred with methanol (660 ml) at room temperature until a fine white solid remained. This was removed by filtration and washed with methanol (100 ml) to give, after drying in vacuo at 60°, 194.8 g of NAG. The filtrate was evaporated to give an oily solid (91.1 g after drying) which was dissolved in water (180 ml). This solution was assayed by ion-exclusion HPLC (cf. Kragl, Gygax, Ghisalba and Wandrey in Angew. Chem. Int. Ed. Eng. Vol.30, 1991, p827–828) and found to contain 205 g/L NAM, 85 g/L NAG (NAM:NAG 2.5:1).

b) The second 1 L portion was mixed with isopropanol (5 L) and left at room temperature for 3 days. The resulting crystals were filtered off (paper), washed with isopropanol (200 ml) and dried in vacuo at 60° to give NAG (159 g). The mother liquors were evaporated to an oily solid which was extracted with methanol (660ml) at room temperature. The residual solid was filtered off and dried in vacuo at 60° (56.4 g). This solid was found still to contain NAM (NAG:NAM c 3:1) sc was re-extracted with methanol to give, after drying, NAG (41.6 g). The filtrate and wash were combined and evaporated to give an oily solid (14.8 g) which was very rich in NAM. This was combined with the oily residue obtained by evaporation of the first filtrate and washes (80.3 g) by dissolving in 167ml of water. Assay of this solution by ion-exclusion HPLC gave 224 g/L NAM, 66 g/L NAG (NAM:NAG 3.4:1).

(ii) Aldolase Reaction

To 20 ml of the NAM-enriched mixture from method b) (4.48 g NAM, 1.32 g NAG) was added sodium pyruvate (4.54 g, 2:1 molar ratio pyruvate:NAM) and enzyme beads (8 g wet weight, from Example 2). The reaction mixture was incubated with stirring at 200 for 48 h.

(iii) Isolation of NANA

At the end of the reaction, the reaction mixture was filtered to remove the enzyme beads and the filtrate (20 ml) was passed through an Amberlite 200 ($H^+$) column (40 ml). NANA was displaced with 1 bv of distilled water, but a further 25 ml was needed to achieve good recovery. The eluate was evaporated back to 20 ml. Acetic acid (5 volumes) was added and the mixture was left at 4° C. for 3 days to crystallise. Needle crystals were removed by filtration and dried in vacuo at 60° to give 3.8 g solid, assaying 95% NANA.

EXAMPLE 5

Production of NANA

Epimerisation and Preparation of NAM-enriched mixtures 5 kg NAG and 110 g sodium hydroxide were dissolved in 12.5 liters of distilled water and the solution allowed to stand at 25° C. After 65 hours 3.3 liters of Amberlite 200 ($H^+$) (Rohm and Haas) was added to reduce the pH below 7.0 and the resin removed by filtration. The epimerised solution contained NAM and NAG in the approximate ratio of 1:4.

NAG was partially crystallised from the epimerised solution by the addition of propan-2-ol (5 volumes), the solid being recovered after 4 days at 4° C. by filtration, and washed with fresh solvent. The propan-2-ol solution was concentrated approximately 6 fold on a Balfors wiped film evaporator giving a second crop of NAG which was recovered by filtration as before. The filtrate was evaporated to dryness on a Buchi rotary evaporator and extracted with a total of 14 liters of methanol. A further crop of NAG was removed at this time. The methanol solution was evaporated to dryness as before, the solid obtained was dissolved to 4.17 liters in water and insoluble material removed by filtration. This solution had a NAM to NAG ratio of approximately 4.5:1.

Bioconversion/Isolation 3.5 liters of the epimerised NAM-enriched mixture (620 g NAM, 133 g NAG) and 442 g of sodium pyruvate were added to a 7 liter vessel. The pH was adjusted to 7.5 with sodium hydroxide and the reaction started by the addition of 1.7 kg of washed immobilised enzyme beads from Example 2. The reaction mixture was stirred at 430 rpm with a single marine impeller, and the temperature maintained at 20° C. The reaction was allowed to proceed for 46 hours after which the enzyme beads were removed from the reaction mixture by vacuum filtration through filter cloth and washed with 1 L distilled water.

NANA was crystallised from the filtrate by the addition of 5 volumes of glacial acetic acid (22.5 L). The solid was recovered after 5 days at 4° C. by vacuum filtration through Whatman 54 paper and washed with fresh acetic acid (4 L). Excess acetic acid was removed from the solid by washing with acetone (24 L) and the solid dried to constant weight at 50° C. in a vacuum oven. Final weight 576.4 g, purity by HPLC 96.4%.

EXAMPLE 6

Production of NANA (i) Epimerisation and Preparation of NAM-enriched mixtures

Sodium hydroxide pellets (5.0 g) were dissolved in process water (1250 ml), NAG (500 g) added and the suspension stirred until solution was obtained. The solution was allowed to stand at 33° C. for 15 hours when the NAM/NAG ratio was 0.21. The solution was neutralised with glacial acetic acid and then concentrated to 986 ml. Six volumes of isopropanol was added and the suspension stirred for 6 hours. Crystallised NAG was filtered off, washed with isopropanol (300 ml) and dried to give 342 g NAG.

(ii) Bioconversion

The combined filtrate and wash (6.30 L) was concentrated to 950 ml, and additional process water added to chase off residual isopropanol. The final concentrate (935 ml) was treated with 86.8 g sodium pyruvate and the pH adjusted to 7.4 with glacial acetic acid. NANA aldolase (40% w/v) was added and the suspension stirred for 25½ hours at 25°.

(iii) Isolation

The enzyme was filtered off and washed with 2×750 ml process water. The filtrate and washes (1.74 L) were concentrated to 395 ml, to which was added with swirling 2370 ml of glacial acetic acid and a small quantity of seed. The crystallised suspension was allowed to stand for 7.5 hours at 21° C. and then filtered. The cake was washed with 118 ml of 85% acetic acid 15% water followed by isopropanol (590 ml) and dried in vacuo at 50° C. The dried solid (90.9 g) assayed at 96.8%.

EXAMPLE 7

Production of NANA Aldolase

*E. coli* TG1[pMexAld] from a freeze dried ampoule was rehydrated using nutrient broth (Oxoid), streaked onto the surface of MGTA agar and incubated at 37° C. overnight. Bacteria from areas of the plate having separate colonies were suspended in Brain Heart Infusion broth (Oxoid) containing 10% glycerol and stored in 0.5 ml amounts at −20° C. for future use.

A 2 liter flask containing 400 ml of MGTA medium (see Example 2) was inoculated with 0.5 ml of stored (−20° C.) suspension and incubated overnight at 37° C. on an orbital shaker (50 mm throw) rotating at 250 rpm. The contents of the flask were used to inoculate a fermenter containing 4.5 L of MGTA. The culture in the fermenter was incubated at 37° C. with aeration at 4.5 L/min and stirring at 500 rpm until a sharp fall in exhaust $CO_2$ concentration indicated the end of logarithmic growth (4.5–6 hours). The contents of the fermenter were used to inoculate a larger vessel containing 450 L of LPSG1 medium maintained at 37° C. with stirring at 350 rpm. The air flow to the vessel was set at 450 L/min and when the exhaust $CO_2$ concentration reached 2% (5–5.5 hr) a solution containing 10.7 g of IPTG (isopropyl β-D-thiogalactoside) was pumped into the fermenter. The culture was harvested 18 hours after inoculation.

| LPSG1 Medium | |
|---|---|
| Ingredients | g/L |
| Lab Lemco Powder (Oxoid) | 40 |
| Peptone L37 (Oxoid) | 40 |
| NaCl | 5 |
| Glycol | 50 |

The cell paste was further treated as described in Example 2.

EXAMPLE 8

Production of NANA Aldolase

*E. coli* TG1[$pP_L$Ald] from a freeze dried ampoule was rehydrated using nutrient broth (Oxoid), streaked onto the surface of nutrient agar (Oxoid) containing 5 mg/L of tetracycline hydrochloride and incubated at 30° C. overnight. Bacteria from areas of the plate having separate colonies were suspended in Brain Heart Infusion broth (Oxoid) containing 10% glycerol and stored in 1 ml amounts at −20° C. for future use.

A 2 liter flask containing 400 ml of MCGTT medium was inoculated with 0.8 ml of stored (−20° C.) suspension and incubated overnight at 30° C. on an orbital shaker (50 mm throw) rotating at 250 rpm. The contents of the flask were used to inoculate a fermenter containing 450 L of LPSG1 (see Example 7) medium maintained at 30° C. with stirring at 200 rpm and an air flow of 450 L/min. After 9 hours, the fermentation temperature was raised to 42° C. to induce aldolase production. The culture was harvested 24 hours after inoculation.

| MCGTT Medium | |
| --- | --- |
| Ingredients | g/L |
| $K_2HPO_4$ | 7 |
| $K_2HPO_4$ | 3 |
| $MgSO_4.7H_2O$ | 0.1 |
| $(NH_4)_2SO_4$ | 1 |
| Tri-sodium citrate | 0.5 |
| Casamino Acids (Difco) | 20 |

Dissolve in distilled water. Natural pH. Sterilise at 121° C. for 15 min.

Added post-autoclaving

| Solution | Conc. (g/L) | Sterilisation | Volume (ml/L) | Final conc. (g/L) |
| --- | --- | --- | --- | --- |
| Glucose | 400 | 121° C. 15 min | 10 | 4 |
| Thiamine.HCl | 1 | Filtration | 2 | 0.002 |
| Tetracycline.HCl | 2.5 | Filtration | 2 | 0.005 |

Freshly-prepared tetracycline solutions were added to the medium immediately before inoculation.

The cell paste was further treated as described in Example 2.

EXAMPLE 9

Production of NANA (i) Epimersation

Sodium hydroxide pellets (1.96 g) were dissolved in water (490 ml), NAG (196 g 7th cycle of use) was added and the suspension stirred until solution was obtained. The solution was allowed to stand at 33< C. for 19 hours when the NAM/NAG ratio was 0.21. The solution was neutralised with glacial acetic acid.

(ii) NAM/NAG Enrichment

The solution was concentrated to 380 mis (0.63 of its original volume). Six volumes of isopropanol (2280 ml) were added and the suspension stirred for 5.5 hours (NAM/NAG ratio 2.14). Crystallised NAG was filtered off, and washed with isopropanol (196 ml) and dried in a vacuum oven at 50° C. overnight to give NAG (130.1 g).

(iii) Bioconversion

The combined filtrate and wash (2660 ml) from NAG filtration was concentrated to 345 ml, and additional process water added to chase off residual isopropanol. The final concentrate (300 ml NAM concentration 90.5 g/l) was treated with sodium pyruvate (27.12 g) (2.15 M sodium pyruvate:1 M NAM) and the pH adjusted to 7.4 with glacial acetic acid. NANA aldolase was added and the suspension stirred for 24 hours at 25° C., this resulting in a conversion of 90%.

(iv) Isolation

The enzyme was filtered off and washed with water (240 ml). The filtrate and washes (590 ml) were concentrated to 136 ml, to which was added with mixing 816 ml (6 vols) of glacial acetic acid and a small quantity of seed. The crystallised suspension was allowed to stand for 17 hours at 21° C. and then filtered. The cake was washed with 41 ml (0.3 vol of 85% acetic acid 15% water followed by acetone (204 mls-1.5 vol). The wet cake (62.93 g) was then used for subsequent work.

(v) Acetone Desolvation

Wet cake (30 g) was added to 0.5% aqueous acetone (268 ml) and the suspension was stirred at room temperature (21° C.) for 2 hours, and then filtered. The cake was washed with acetone (2×40 mls), and dried in a vacuum oven at 50° C. overnight to give desolvated NANA (12.44 g) (Potency 99.2%, corrected for water content).

(vi) Rhomboid Crystallisation

Wet cake (30 g) was added slowly to water (27 mls) whilst stirring. The suspension was stirred for 30 minutes at 21° C., by which time the wet cake had converted to rhomboids. Acetone (240 mls) was added over 30 minutes. After acetone addition the mixture was stirred for 1.5 hours at 21° C. The mixture was then cooled to 5° C. for 1 hour and filtered. The cake was washed with acetone (2×40 mls), and dried in a vacuum oven at 35° C. overnight to give NANA rhomboids (13.44 g). (Potency 99.4%, corrected for water content).

EXAMPLE 10

Crystallisation of Rhomboid Crystals

N-Acetyl-D-Neuraminic rhomboid crystals (56 g) were added to stirred water (100 ml) at room temperature over 25–30 minutes. Initially solution occurred but rhomboid crystals later precipitated. The slurry was stirred for 30 minutes and acetone (800 mls) added over 30 minutes. The slurry was stirred for 2 hours at room temperature. The solids were filtered, washed with a acetone water mixture (8:1, 100 ml) followed by acetone (300 ml) and dried in vacuo at 35° C. overnight. Yield solid, 94.1% w/w.

What is claimed is:

1. A process for the preparation of N-acetyl-D-neuraminic acid (NANA), said process comprising the steps of:
   1. converting N-acetyl-D-glucosamine (NAG) to N-acetyl-D-mannosamine (NAM) by base-catalyzed epimerization to yield an equilibrium mixture of NAG/NAM;
   2. selectively removing NAG from the equilibrium mixture;
   3. reacting NAM with pyruvate in the presence of NANA aldolase; and
   4. isolating the thus-produced NANA, by crystallization from the reaction mixture;
   wherein the pyruvate:NAM starting molar ratio for step 3 is about 1.5:1 to 2.5:1.

2. A process as claimed in claim 1 wherein epimerization is carried out at the saturation concentration of NAG.

3. A process as claimed in claim 1 wherein the reaction mixture is neutralized prior to the third step.

4. A process as claimed in claim 1 wherein removal of NAG is effected by treatment of the NAM/NAG mixture with an organic solvent and removal of crystalline NAG.

5. A process as claimed in claim 4 wherein the organic solvent is ;a lower alcohol.

6. A process as claimed in claim 4 wherein the organic solvent is isopropanol.

7. A process as claimed in claim 6 wherein the ratio of isopropanol to the NAM/NAG mixture is 5:1 to 10:1.

8. A process as claimed in claim 6 further enrichment is effected by evaporation of the isopropanol/water azeotrope.

9. A process as claimed in claim 6 wherein the enrichment effected at a temperature of from 15° to 30° C.

10. A process as claimed in claim 1 wherein crystallization of NANA from the reaction mixture is effected by addition of from 4 to 8 volumes of acetic acid.

11. A process as claimed in claim 1 wherein the NAG removed from the NAM/NAG mixture is reused in step 1 of the process.

12. A process as claimed in claim 1 wherein the NANA aldolase is obtained from an over-expressing recombinant strain of E. coli.

13. A process as claimed in claim 12 wherein the recombinant strain of E. coli is TG1[pPLAld].

14. A process as claimed in claim 1 wherein the NANA aldolase is immobilized.

15. A process as claimed in claim 1 wherein step 3 is effected at pH 6 to 9 and temperature 5° to 60° C.

16. A process as claimed in claim 1 wherein NANA is isolated as needle-shaped crystals.

17. A process as claimed in claim 1 wherein NANA is isolated as rhombic crystals.

18. A process for the preparation of N-acetyl-D-neuraminic acid (NANA), said process comprising the steps of:
   1. converting N-acetyl-D-glucosamine (NAG) to N-acetyl-D-mannosamine (NAM) by base-catalyzed epimerization to yield an equilibrium mixture of NAG/NAM;
   2. selectively removing NAG from the equilibrium mixture;
   3. reacting NAM with pyruvate in the presence of NANA aldolase; and
   4. isolating the thus-produced NANA, by crystallization from the reaction mixture;

wherein removal of NAG in step 2 is effected by treatment of the NAM/NAG mixture with isopropanol and removal of crystalline NAG, the pyruvate:NAM starting molar ratio for step 3 is about 1.5:1 to 2.5:1, the NANA aldolase in step 3 is obtained from an over expressing recombinant strain of *E. Coli,* and is immobilized, and crystallization of NANA from the reaction mixture in step 4 is effected by addition of from 4 to 8 volumes of acetic acid.

19. A process as claimed in claim 1, further comprising the addition of acetone to an aqueous solution of NANA and wherein the NANA is isolated as rhombic crystals.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 3985 base pairs
      (B) TYPE: nucleic acid
      (C) STRANDEDNESS: single
      (D) TOPOLOGY: linear (xi) SEQUENCE DESCRIPTION: SEQ ID NO:1:

```
AATTCTTACA CTTAGTTAAA TTGCTAACTT TATAGATTAC AAAACTTAGG AGGGTTTTTA      60

CCATGGTACC TTTAAACCCG GGTCGACGGA TCCTGCAGCC CAGCTTGGGG ACCCTAGAGG     120

TCCCCTTTTT TATTTTGAAT TGGGAGATCC CAATTCTCAT GTTTGACAGC TTATCATCGA     180

TAAGCTAGCT TTAATGCGGT AGTTTATCAC AGTTAAATTG CTAACGCAGT CAGGCACCGT     240

GTATGAAATC TAACAATGCG CTCATCGTCA TCCTCGGCAC CGTCACCCTG GATGCTGTAG     300

GCATAGGCTT GGTTATGCCG GTACTGCCGG GCCTCTTGCG GGATATCGTC CATTCCGACA     360

GCATCGCCAG TCACTATGGC GTGCTGCTAG CGCTATATGC GTTGATGCAA TTTCTATGCG     420

CACCCGTTCT CGGAGCACTG TCCGACCGCT TTGGCCGCCG CCCAGTCCTG CTCGCTTCGC     480

TACTTGGAGC CACTATCGAC TACGCGATCA TGGCGACCAC ACCCGTCCTG TGGATTCTCT     540

ACGCCGGACG CATCGTGGCC GGCATCACCG GCGCCACAGG TGCGGTTGCT GGCGCCTATA     600

TCGCCGACAT CACCGATGGG GAAGATCGGG CTCGCCACTT CGGGCTCATG AGCGCTTGTT     660

TCGGCGTGGG TATGGTGGCA GGCCCCGTGG CCGGGGGACT GTTGGGCGCC ATCTCCTTGC     720

ACGCACCATT CCTTGCGGCG GCGGTGCTCA ACGGCCTCAA CCTACTACTG GGCTGCTTCC     780

TAATGCAGGA GTCGCATAAG GGAGAGCGTC GTCCGATGCC CTTGAGAGCC TTCAACCCAG     840

TCAGCTCCTT CCGGTGGGCG CGGGGCATGA CTATCGTCGC CGCACTTATG ACTGTCTTCT     900

TTATCATGCA ACTCGTAGGA CAGGTGCCGG CAGCGCTCTG GGTCATTTTC GGCGAGGACC     960

GCTTTCGCTG GAGCGCGACG ATGATCGGCC TGTCGCTTGC GGTATTCGGA ATCTTGCACG    1020

CCCTCGCTCA AGCCTTCGTC ACTGGTCCCG CCACCAAACG TTTCGGCGAG AAGCAGGCCA    1080

TTATCGCCGG CATGGCGGCC GACGCGCTGG GCTACGTCTT GCTGGCGTTC GCGACGCGAG    1140

GCTGGATGGC CTTCCCCATT ATGATTCTTC TCGCTTCCGG CGGCATCGGG ATGCCCGCGT    1200

TGCAGGCCAT GCTGTCCAGG CAGGTAGATG ACGACCATCA GGGACAGCTT CAAGGATCGC    1260

TCGCGGCTCT TACCAGCCTA ACTTCGATCA CTGGACCGCT GATCGTCACG GCGATTTATG    1320

CCGCCTCGGC GAGCACATGG AACGGGTTGG CATGGATTGT AGGCGCCGCC CTATACCTTG    1380

TCTGCCTCCC CGCGTTGCGT CGCGGTGCAT GGAGCCGGGC CACCTCGACC TGAATGGAAG    1440

CCGGCGGCAC CTCGCTAACG GATTCACCAC TCCAAGAATT GGAGCCAATC AATTCTTGCG    1500

GAGAACTGTG AATGCGCAAA CCAACCCTTG GCAGAACATA TCCATCGCGT CCGCCATCTC    1560

CAGCAGCCGC ACGCGGCGCA TCTCGGGGGA TGATCAGCTG CCTCGCGCGT TTCGGTGATG    1620

ACGGTGAAAA CCTCTGACAC ATGCAGCTCC CGGAGACGGT CACAGCTTGT CTGTAAGCGG    1680

ATGCCGGGAG CAGACAAGCC CGTCAGGCGC CGTCAGCGGG TGTTGGCGGG TGTCGGGGCG    1740

CAGCCATGAC CCAGTCACGT AGCGATAGCG GAGTGTATAC TGGCTTAACT ATGCGGCATC    1800

AGAGCAGATT GTACTGAGAG TGCACCATAT GCGGTGTGAA ATACCGCACA GATGCGTAAG    1860
```

-continued

```
GAGAAAATAC CGCATCAGGC GCTCTTCCGC TTCCTCGCTC ACTGACTCGC TGCGCTCGGT     1920

CGTTCGGCTG CGGCGAGCGG TATCAGCTCA CTCAAAGGCG GTAATACGGT TATCCACAGA     1980

ATCAGGGGAT AACGCAGGAA AGAACATGTG AGCAAAAGGC CAGCAAAAGG CCAGGAACCG     2040

TAAAAAGGCC GCGTTGCTGG CGTTTTTCCA TAGGCTCCGC CCCCCTGACG AGCATCACAA     2100

AAATCGACGC TCAAGTCAGA GGTGGCGAAA CCCGACAGGA CTATAAAGAT ACCAGGCGTT     2160

TCCCCCTGGA AGCTCCCTCG TGCGCTCTCC TGTTCCGACC CTGCCGCTTA CCGGATACCT     2220

GTCCGCCTTT CTCCCTTCGG GAAGCGTGGC GCTTTCTCAA TGCTCACGCT GTAGGTATCT     2280

CAGTTCGGTG TAGGTCGTTC GCTCCAAGCT GGGCTGTGTG CACGAACCCC CCGTTCAGCC     2340

CGACCGCTGC GCCTTATCCG GTAACTATCG TCTTGAGTCC AACCCGGTAA GACACGACTT     2400

ATCGCCACTG GCAGCAGCCA CTGGTAACAG GATTAGCAGA GCGAGGTATG TAGGCGGTGC     2460

TACAGAGTTC TTGAAGTGGT GGCCTAACTA CGGCTACACT AGAAGGACAG TATTTGGTAT     2520

CTGCGCTCTG CTGAAGCCAG TTACCTTCGG AAAAAGAGTT GGTAGCTCTT GATCCGGCAA     2580

ACAAACCACC GCTGGTAGCG GTGGTTTTTT TGTTTGCAAG CAGCAGATTA CGCGCAGAAA     2640

AAAAGGATCT CAAGAAGATC CTTTGATCTT TTCTACGGGG TCTGACGCTC AGTGGAACGA     2700

AAACTCACGT TAAGGGATTT TGGTCATGAG ATTATCAAAA AGGATCTTCA CCTAGATCCT     2760

TTTCAGATCT CCCGATCTTT AGCTGTCTTG GTTTGCCCAA AGCGCATTGC ATAATCTTTC     2820

AGGGTTATGC CTTGTTCCAT ACAACCTCCT TAGTACATGC AACCATTATC ACCGCCAGAG     2880

GTAAAATAGT CAACACGCAC GGTGTTAGAT ATTTATCCCT TGCGGTGATA GATTTAACGT     2940

ATGAGCACAA AAAAGAAACC ATTAACACAA GAGCAGCTTG AGGACGCACG TCGCCTTAAA     3000

GCAATTTATG AAAAAAAGAA AAATGAACTT GCGTTATCCC AGGAATCTGT CGCAGACAAG     3060

ATGGGGATGG GGCAGTCAGG CGTTGGTGCT TTATTTAATG GCATCAATGC ATTAAATGCT     3120

TATAACGCCG CATTGCTTAC AAAAATTCTC AAAGTTAGCG TTGAAGAATT TAGCCCTTCA     3180

ATCGCCAGAG AAATCTACGA GATGTATGAA GCGGTTAGTA TGCAGCCGTC ACTTAGAAGT     3240

GAGTATGAGT ACCCTGTTTT TTCTCATGTT CAGGCAGGGA TGTTCTCACC TAAGCTTAGA     3300

ACCTTTACCA AAGGTGATGC GGAGAGATGG GTAAGCACAA CCAAAAAAGC CAGTGATTCT     3360

GCATTCTGGC TTGAGGTTGA AGGTAATTCC ATGACCGCAC CAACAGGCTC CAAGCCAAGC     3420

TTTCCTGACG GAATGTTAAT TCTCGTTGAC CCTGAGCAGG CTGTTGAGCC AGGTGATTTC     3480

TGCATAGCCA GACTTGGGGG TGATGAGTTT ACCTTCAAGA AACTAATTAG GGATAGCGGT     3540

CAGGTGTTTT TACAACCACT AAACCCACAG TACCCAATGA TCCCATGCAA TGAGAGTTGT     3600

TCCGTTGTGG GGAAAGTTAT CGCTAGTCAG TGGCCTGAAG AGACGTTTGG CTGATCGGCA     3660

AGGTGTTCTG GTCGGCGCAT AGCTGATAAC AATTGAGCAA GAATCTTCAT CGGGGCTGCA     3720

GCCCACGATG CGTCCGGCGT AGAGGATCTC TCACCTACCA AACAATGCCC CCTGCAAAA     3780

AATAAATTCA TATAAAAAAC ATACAGATAA CCATCTGCGG TGATAAATTA TCTCTGGCGG     3840

TGTTGACATA AATACCACTG GCGGTGATAC TGAGCACATC AGCAGGACGC ACTGACCACC     3900

ATGAAGGTGA CGCTCTTAAA ATTAAGCCCT GAAGAAGGGC AGCATTCAAA GCAGAAGGCT     3960

TTGGGGTGTG TGATACGAAA CGAAG                                           3985
```

(2) INFORMATION FOR SEQ ID NO:2:

(i) SEQUENCE CHARACTERISTICS:
        (A) LENGTH: 902 base pairs
        (B) TYPE: nucleic acid (C) STRANDEDNESS: single
            (D) TOPOLOGY: linear (xi) SEQUENCE DESCRIPTION: SEQ ID NO:2:

CCATGGCAAC GAATTTACGT GGCGTAATGG CTGCACTCCT GACTCCTTTT GACCAACAAC        60

AAGCACTGGA TAAAGCGAGT CTGCGTCGCC TGGTTCAGTT CAATATTCAG CAGGGCATCG       120

ACGGTTTATA CGTGGGTGGT TCGACCGGAG AGGCCTTTGT ACAAAGCCTT TCCGAGCGTG       180

AACAGGTACT GGAAATCGTC GCCGAAGAGG CGAAAGGTAA GATTAAACTC ATCGCCCACG       240

TCGGTTGCGT CAGCACCGCC GAAAGCCAAC AACTTGCGGC ATCGGCTAAA CGTTATGGCT       300

TCGATGCCGT CTCCGCCGTC ACGCCGTTCT ACTATCCTTT CAGCTTTGAA GAACACTGCG       360

ATCACTATCG GGCAATTATT GATTCGGCGG ATGGTTTGCC GATGGTGGTG TACAACATTC       420

CAGCCCTGAG TGGGGTAAAA CTGACCCTGG ATCAGATCAA CACACTTGTT ACATTGCCTG       480

GCGTAGGTGC GCTGAAACAG ACCTCTGGCG ATCTCTATCA GATGGAGCAG ATCCGTCGTG       540

AACATCCTGA TCTTGTGCTC TATAACGGTT ACGACGAAAT CTTCGCCTCT GGTCTGCTGG       600

CGGGCGCTGA TGGTGGTATC GGCAGTACCT ACAACATCAT GGGCTGGCGC TATCAGGGGA       660

TCGTTAAGGC GCTGAAAGAA GGCGATATCC AGACCGCGCA GAAACTGCAA ACTGAATGCA       720

ATAAAGTCAT TGATTTACTG ATCAAAACGG GCGTATTCCG CGGCCTGAAA ACTGTCCTCC       780

ATTATATGGA TGTCGTTTCT GTGCCGCTGT GCCGCAAACC GTTTGGACCG GTAGATGAAA       840

AATATCTGCC AGAACTGAAG GCGCTGGCCC AGCAGTTGAT GCAAGAGCGC GGGTGAGTCG       900

AC                                                                   902

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:3:

CGCCGAAGAG GCGAAAGGTA                                                  20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:4:

CCAGCCCTGA GTGGGGTAAA                                                  20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

TGGGCTGGCG CTATCAGGGG                                                  20

(2) INFORMATION FOR SEQ ID NO:6:

```
        (i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:6:

GCGCGGTCTG GATATCGCCT                                                     20

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:7:

AGGCAATGTA ACAAGTGTGT                                                     20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO:8:

GCGGTGCTGA CGCAACCGAC                                                     20
```